United States Patent [19]

Kirk

[11] Patent Number: 5,456,249
[45] Date of Patent: Oct. 10, 1995

[54] RESUSCITATOR WITH CARBON DIOXIDE DETECTOR

[76] Inventor: Gilbert M. Kirk, 2222 Arbor Crest Dr., Carrollton, Tex.

[21] Appl. No.: 177,438

[22] Filed: Jan. 5, 1994

Related U.S. Application Data

[62] Division of Ser. No. 776,615, Oct. 15, 1991, Pat. No. 5,279,289.

[51] Int. Cl.$^6$ ............... A62B 9/02; A62B 7/10; A62B 23/02
[52] U.S. Cl. ............... 128/205.13; 128/205.23; 128/205.24; 128/205.28
[58] Field of Search ............ 128/200.24, 202.22, 128/204.18, 205.12, 205.13, 205.17, 205.23–205.25, 205.28, 202.27–203.11, 203.28, 203.29, 207.12, 207.16

[56] References Cited

U.S. PATENT DOCUMENTS

| | | | |
|---|---|---|---|
| 3,556,122 | 1/1971 | Laerdal | 137/102 |
| 3,612,048 | 10/1971 | Takaoka et al. | 128/188 |
| 3,615,233 | 10/1971 | Doering et al. | 23/252 |
| 4,077,404 | 3/1978 | Elam | 128/205.13 |
| 4,728,499 | 3/1988 | Fehder | 422/56 |
| 4,774,941 | 10/1988 | Cook | 128/205.13 |
| 4,790,327 | 12/1988 | Despotis | 128/719 |
| 4,879,999 | 11/1989 | Leiman et al. | 128/207.14 |
| 4,928,687 | 5/1990 | Lampotang et al. | 128/207.14 |
| 4,945,918 | 8/1990 | Abernathy | 128/719 |
| 4,994,117 | 2/1991 | Fehder | 436/133 |
| 5,005,572 | 4/1991 | Raemer et al. | 128/207.14 |
| 5,109,840 | 5/1992 | Daleiden | 128/205.13 |
| 5,124,129 | 1/1992 | Riccitelli et al. | 422/56 |
| 5,179,002 | 1/1993 | Fehder | 435/25 |

FOREIGN PATENT DOCUMENTS

| | | | |
|---|---|---|---|
| 0139363 | 5/1985 | European Pat. Off. | 128/205.13 |
| 3818783 | 12/1989 | Germany | 128/205.23 |
| 2139099 | 11/1984 | United Kingdom | 128/205.13 |
| 8907956 | 9/1989 | WIPO | 128/207.14 |
| 8907957 | 9/1989 | WIPO | 128/207.14 |

*Primary Examiner*—Kimberly L. Asher
*Attorney, Agent, or Firm*—Baker & Botts

[57] ABSTRACT

A resuscitator is provided with an integral carbon dioxide detector for indicating the presence of carbon dioxide in a patient. The carbon dioxide detector is a conventional pH sensitive chromogenic compound that is positioned in the breathing circuit to permit a rapid indication. Additionally, a unique plug is provided for sealing the indicator from the atmosphere while in storage to prevent contamination and degradation of the indicator compound.

8 Claims, 5 Drawing Sheets

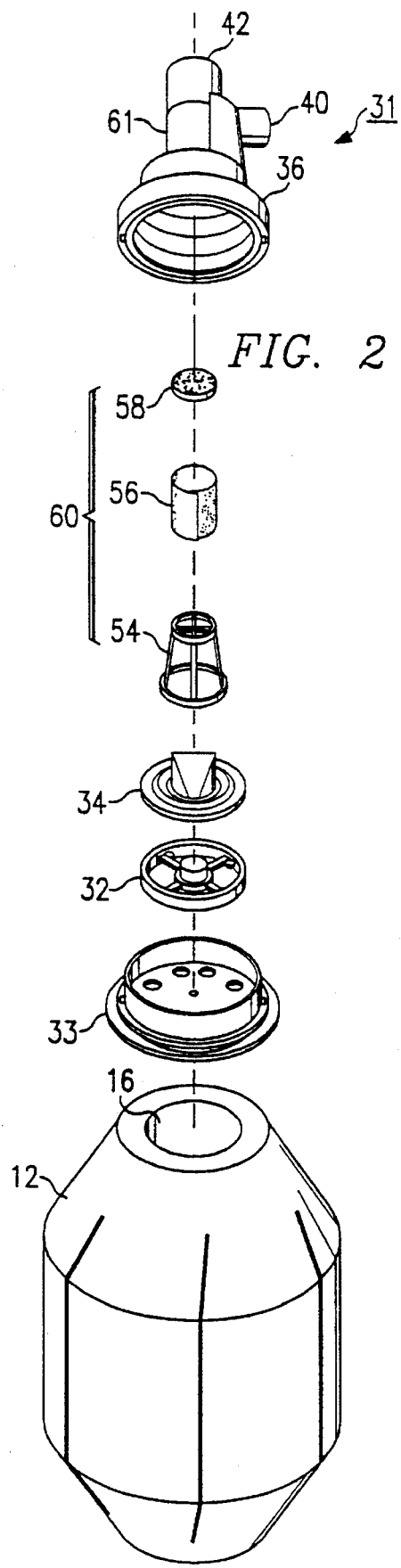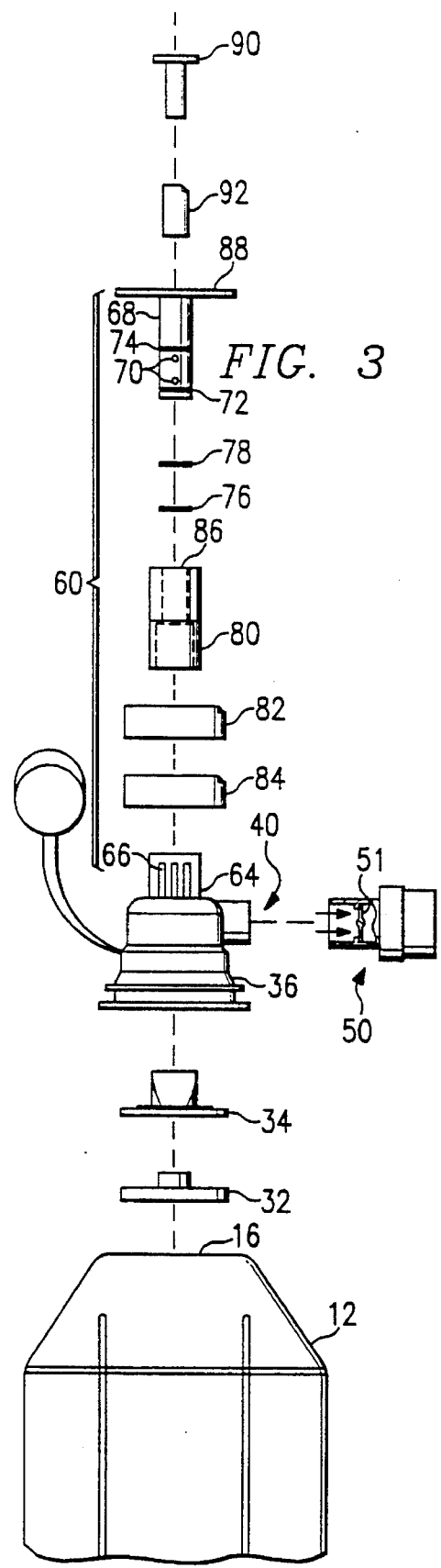

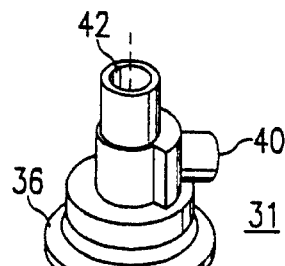
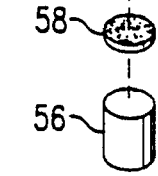
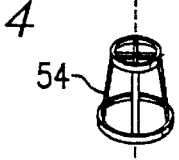
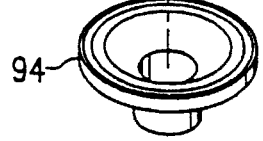
FIG. 4
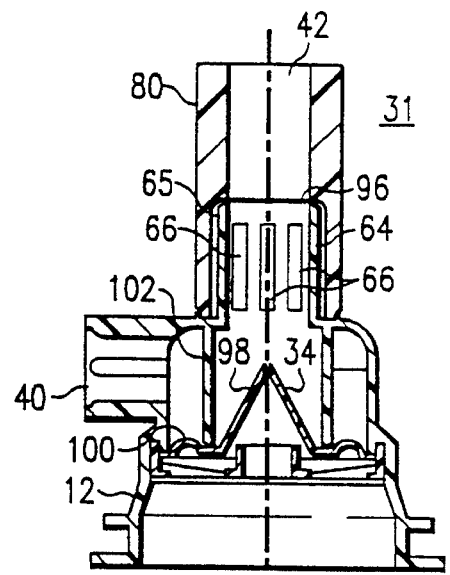
FIG. 5
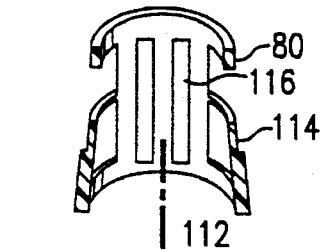
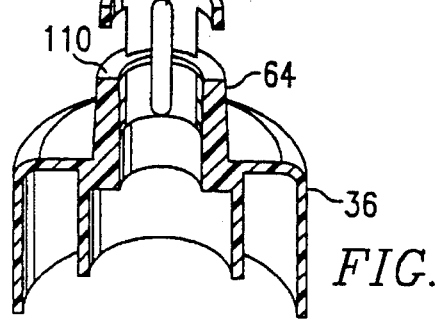
FIG. 7
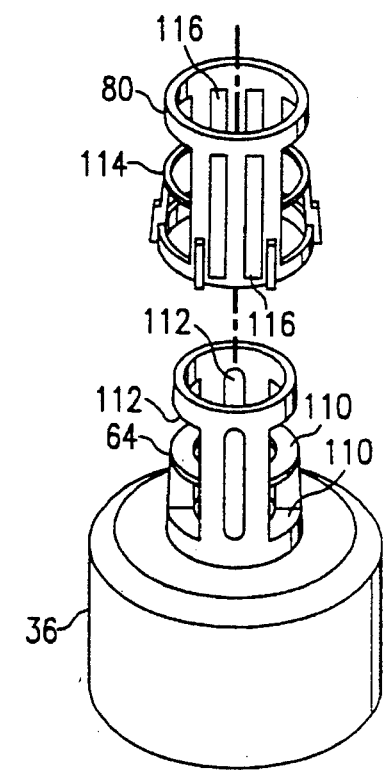
FIG. 6

RESUSCITATOR WITH CARBON DIOXIDE DETECTOR

CROSS REFERENCE TO RELATED APPLICATIONS

This application is a divisional application of U.S. application Ser. No. 07/776,615, filed Oct. 15, 1991, now U.S. Pat. No. 5,279,289 and entitled "RESUSCITATOR REGULATOR WITH CARBON DIOXIDE DETECTOR" by Gilbert M. Kirk.

TECHNICAL FIELD OF THE INVENTION

The invention relates generally to the field of medical devices. Specifically the invention relates to a resuscitator and more particularly to a resuscitator with a carbon dioxide detector.

BACKGROUND OF THE INVENTION

Manual resuscitators for use with patients either unable to breathe on their own or needing assistance are well known in the prior art. An example of a prior art resuscitator is described in U.S. Pat. No. 4,774,941 to Cook. A typical prior art resuscitator comprises a resuscitator bag for mechanically forcing oxygen or air into the patient, a regulator for controlling the flow of inhalation and exhalation gasses, and a means for connecting the resuscitator to the patient such as a facemask or intubation tube.

A serious problem in the resuscitation of patients is the inability to determine whether the patient is respirating. It is difficult for the medical professional using the resuscitator to determine whether the patient is receiving an adequate flow of oxygen. For example, something may be blocking the patient's trachea preventing oxygen air exchange or, in the case of an endotrachial tube, the tube may be inserted into the patient's esophagus. Therefore, a need has arisen for an efficient and economical way of determining whether the patient being treated with a resuscitator is actually receiving oxygen.

One way of determining whether a patient is receiving oxygen is to detect the presence of $CO_2$ in the exhalation gasses. The normal atmospheric concentration of $CO_2$ is less than 0.5%. So, presence of $CO_2$ in excess of that amount is generally a strong indication that the patient is receiving oxygen and performing some respiration. Carbon dioxide detectors using a chromogenic pH-sensitive indicator are well known in the prior art. An example of such an indicator is described in U.S. Pat. Nos. 4,728,499 and 4,994,117 to Fehder. These carbon dioxide indicators are of the type that need to be connected between the patient and the resuscitator. This limitation has numerous and significant disadvantages. First, the medical professional is required to install the device before he or she can begin resuscitating the patient. In many instances, resuscitation occurs in emergency situations making such a device unattractive to the medical professional. Second, the connection of the carbon dioxide indicator adds additional volume to the breathing circuit increasing the trapping of exhaled gasses and other material. In that instance, the patient is no longer receiving fresh oxygenated air but is rebreathing his or her own exhaled gasses. This is particularly troublesome when using resuscitators on infants whose lung capacity is much smaller than those of adults. Third, since the carbon dioxide detector requires its own housing and connector ports, the expense is significantly increased over what it would be if the detector were contained integral with the resuscitator.

Therefore, a need has arisen to combine a carbon dioxide detector in a resuscitator. This need has been long recognized by the medical profession and numerous attempts have been made to design a resuscitator that integrates a carbon dioxide detector. An example of such device is disclosed in U.S. Pat. No. 4,945,918 to Abernathy. The apparatus disclosed in the Abernathy patent suffers from some of the same disadvantages described before. In particular, the Abernathy device requires assembly by the medical professional that is both cumbersome and time consuming. Another disadvantage of the Abernathy device is that the indicator is not directly incorporated in the resuscitator and is not located in the direct breathing circuit. Another disadvantage of the Abernathy device is that by failing to place the carbon dioxide detector in the direct breathing circuit, the indicator may not be cleansed with fresh air after each resuscitation and therefore accuracy of the indicator is sacrificed. Another disadvantage of the Abernathy device is that the indicator requires a four minute period to indicate whether carbon dioxide is present. These and other disadvantages of the prior art are overcome by the device of the present invention.

SUMMARY OF THE INVENTION

The resuscitator of the present invention comprises a flexible container, a regulator and a means for detecting carbon dioxide. The flexible container or bag supplies fresh air or gas containing oxygen to the patient. The container has an inlet opening for admitting the fresh air and an outlet opening for conveying the fresh air to the patient. The regulator is fixed to the outlet opening of the container and has an inhalation port, an exhalation port and a viewing window. The regulator further comprises a control valve located over the outlet opening of the container for controlling the flow of fresh air to the patient through the inhalation port. The carbon dioxide detecting means is located in the viewing window of the housing and is for detecting the presence of carbon dioxide in the exhaled gas from the patient before entering the exhalation port.

A technical advantage of the present invention is that a resuscitator is provided having an integrated carbon dioxide detector that avoids the need for assembly by the medical professional and provides a rapid response for detecting the proper functioning of the resuscitator. Another technical advantage of the present invention is that the carbon dioxide detector is in the direct breathing circuit providing for a more accurate indication of respiration and reducing the quantity of volume that may contain stale air. Another technical advantage of the present invention is that a rapid response $CO_2$ indicator is integrated in the breathing circuit of a resuscitator to provide a medical professional with almost an instantaneous indication that respiration is taking place.

BRIEF DESCRIPTION OF THE DRAWINGS

For a more complete understanding of the present invention and the advantages thereof, reference is now made to the following description taken in conjunction with the accompanying drawings, in which:

FIG. 1A shows a tube and connector for use with the resuscitator of the present invention;

FIG. 2 is an exploded view illustrating one embodiment of the present invention;

FIG. 3 is an exploded view illustrating a second embodiment of the present invention;

FIG. 4 is a regulator for use in connection with the present invention;

FIG. 5 is a sectional view of a regulator for use in connection with the present invention;

FIG. 6 is an alternative embodiment of an indicator assembly for use with the invention;

FIG. 7 is a section view of the indicator assembly shown in FIG. 6;

DETAILED DESCRIPTION OF THE INVENTION

Figure 1:
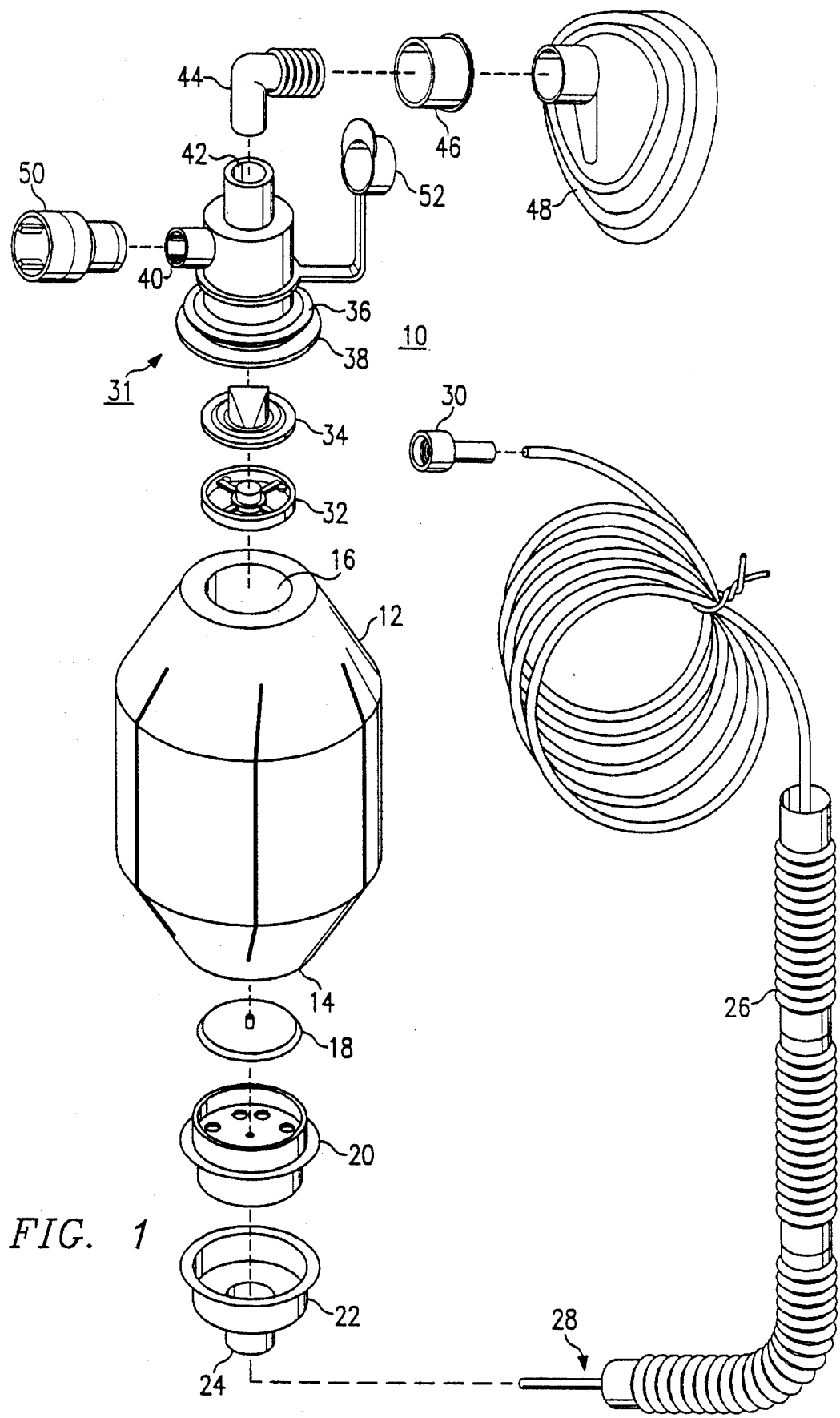
FIG. 1 illustrates a resuscitator of the prior art suitable for use with the present invention.

Referring now to FIG. 1, a resuscitator made in accordance with the present invention is described. Resuscitator 10 has a container or bag 12 with inlet opening 14 and outlet opening 16. Attached to inlet opening 14 of container 12 is rear housing assembly 17 comprised of diaphragm valve 18, diaphragm valve support 20 and housing cap 22. Diaphragm valve 18 is attached to diaphragm valve support 20 to prevent flow of air out of container 12. Housing cap 22 has an entrance 24 providing for the flow of fresh air through diaphragm valve 18 to the patient. Alternatively, tube 26 may be connected to housing entrance 24 via connector 28 which may at the opposite end, via universal connector 30, be connected to a supply of oxygen.

By manually squeezing and releasing repetitively flexible bag 12, fresh air is pumped through entrance 24 and passed by diaphragm valve 18 through outlet opening 16. Connected to outlet opening 16 of resuscitator 10 is a retainer ring 32 which is positioned over outlet opening 16 to support valve 34. In the preferred embodiment, valve 34 is a duckbill valve which is amply described in U.S. Pat. No. 3,556,122 to Laerdal. Fitted over outlet opening 16 and connected to bag 12 by suitable means well know to those skilled in the art is regulator 31 comprised of a housing 36. Housing 36 has an inlet opening 38 in which is positioned retainer ring 32 and control valve 34. Housing 36 also has an exhalation port 40 and an inhalation port 42. Inhalation port 42 is connected to elbow 44 that communicates through adapter 46 to facemask 48. Facemask 48 is positioned over the mouth and nostrils of a patient being resuscitated. Exhalation port 40 may also have associated adapter 50 for communicating with the atmosphere. Also attached to housing 36 is cap 52 for affixing over inhalation port 42 when resuscitator 10 is not in use.

Referring now to FIG. 2, the regulator 31 is described in more detail showing the carbon dioxide detector for use in the present invention. Fixed over valve 34 is frame 54 for supporting indicator element 56. In the preferred embodiment, indicator element 56 is contructed of a fiberous material that acts as a carrier for a pH sensitive chromogenic compound. In the preferred embodiment, the indicator element is impregnated with an aqueous solution of a colorless compound such as a base which provides an alkaline solution. Indicator element 56 further comprises a hygro-scopic, high boiling point, transparent, colorless, water-miscible liquid which changes color relative to a change in pH of the solution and which has a pH which is lower by 1.0–1.5 pH units than the pH of the solution. The nature and concentration of the colorless compound is correlated to the nature and concentration of the indicator so that no color change occurs for at least fifteen minutes when the indicating element is exposed to an atmosphere having a concentration of 0.03% carbon dioxide, but a color change is produced within five to ten seconds when the indicating element is exposed to a gas containing at least two percent carbon dioxide. PH sensitive chromogenic carbon dioxide indicators are well known to those skilled in the art. Examples of suitable indicators and the method for making them is described in U.S. Pat. Nos. 4,728,499 and 4,994,117 to Fehder and U.S. Pat. No. 5,005,572 to Raemer et al. These patents teach formulas for carbon dioxide indicators that will change color in proportion to the concentration of $CO_2$ which indicates the efficiency of the patient's respiration.

Still referring to FIG. 2, indicator element 56 is placed over frame 54 and capped by filter 58. Housing 36 then fits over the indicator assembly 60 and is held in place by internal shoulders positioned inside inhalation port 42 that asserts downward pressure on filter 58.

The housing 36 of regulator 31 in the preferred embodiment is constructed of a clear polymeric material such as acrylic. In an alternative embodiment, housing 36 is constructed of an opaque polymeric material with a clear window 62 that permits the viewing of indicator element 56. Window 62 can be coded so that as indicator element 56 changes colors, the color change indicates the concentration of carbon dioxide in the stale exhaled gas from the patient.

Referring now to FIG. 3, an alternative embodiment of regulator 31 is described in combination with a plug for sealing the carbon dioxide detector from the atmosphere during storage. In this embodiment, valve 34 is fitted over retainer 32 that is affixed to housing 36. Housing 36 is attached to bag 12 as has been previously described. In this embodiment, exhalation port 40 of housing 36 has an inner frame 64 that has perforations 66 for permitting the freeflow of gas through indicator assembly 60. In this embodiment, indicator assembly 60 comprises a plug 68 having holes 70 and recesses 72 and 74. Recess 72 cooperates with O-ring 76 and recess 74 cooperates with O-ring 78 to form a seal against the inside of innerframe 64. Cap 80 fits over innerframe 64 and cooperates with indicator strip 82 and filter strip 84. Filter barrier 84 is fitted around innerframe 64 and held in place by adhesive material not shown but well known to those skilled in the art. Around filter barrier 84 indicator strip 82 is placed and held in position by similar adhesive strips not shown. In an alternative embodiment, filter barrier 84 and indicator strip are held in place by a friction fit. Fitted over indicator strip 82 is cap 80 which is sealed into position by suitable means.

In the embodiment depicted in FIG. 3, exhalation gas flows through opening 86 of cap 80 and is then passed through perforations 66 exposing chemically impregnated indicator strip 82 to the exhaled patient gasses. Depending upon the concentration of $CO_2$ contained in the exhalation gasses, a color change takes place, as previously described, that indicates the presence of carbon dioxide. When the patient is respirated or during insufflation, fresh air passes across and through inner frame 64 and through perforations 66 to cleanse indicator strip 82 and change the color back to neutral. The exhaled gasses then pass through exhalation port 40 to adapter 50 provided with one-way flapper valve 51 for preventing the backflow of air into the device. In this way, each patient exhalation provides a new indication as to the condition of the patient's respiratory system and his ability to absorb oxygen and exhale carbon dioxide.

In the embodiment depicted in FIG. 3, a unique cap and plug are provided for sealing indicator strip 82 from the atmosphere while in storage or not in use. While most chemical indicators will not change color when exposed to atmospheric carbon dioxide for short periods of time, they will degrade over the course of time and ultimately be unusable. Thus, it is necessary to provide a means for sealing the indicator from the atmosphere while not in use. Numerous alternatives have been described in the prior art such as foil pull tabs and sealing pouches, but all have the disadvantage of requiring disassembly and are susceptible to puncture as well as other disadvantages. Referring to FIG. 3, cap 68 is inserted in innerframe 64. By employing O-rings 76 and 78, indicator element 82 is isolated top and bottom from the atmosphere. In this way, the only way for air or gas to reach indicator element 82 is through holes 70 of cap 68. Aperture 88 of cap 68 is fitted for plug 90 which is inserted and seals against the internal walls of cap 68. Also inserted before plug 90 is absorber 92 which in the preferred embodiment is a material impregnated with soda lime for absorbing carbon dioxide. In this way, indicator strip 82 is completely isolated from the atmosphere and will not become degraded over time. When it becomes necessary to use the resuscitator, plug 90 is removed along with absorber 92 and the resuscitation device is ready for use on a patient.

Referring now to FIG. 4, another embodiment of the present invention is shown in the form of a regulator adaptable for connection in a breathing circuit including a resuscitator. Regulator 31 comprises a housing 36 having an inlet 38, an exhalation port 40 and an inhalation port 42. Adjacent and opposite exhalation port 40 is clear window 61 for permitting the observation of a carbon dioxide indicator element. Filter 58 is placed across the opening of inhalation port 42 to prevent exhaled materials such as saliva and the like from fouling indicator element 56. Indicator element 56 is fitted over frame 54 that attaches to valve 34 supported by retention ring 32. The entire indicator assembly and valve and retention ring mechanism is sealed in regulator 31 by means of housing 36 and cap 94.

Referring now to FIG. 5, a cross-sectional view of the preferred embodiment of regulator 31 affixed to a resuscitator bag 12 is described. Regulator housing 36 has inner frame 64 with perforations 66. Sandwiched between innerframe wall 65 and cap 80 but not shown in this figure would be indicator element 82 and filter element 84. Cap 80 fits snuggly over inner frame 64 so that an air tight seal is created at seam 96. When bag 12 is squeezed, air is forced through valve 34 and out through opening 42 of cap 80. When the patient exhales, the force of the exhalation gasses pushes against the outside flaps 98 of valve 34 creating an opening between annular space 100 and housing wall 102. Thus, the exhalation gasses can pass through inhalation port 42 around valve 34 and out through exhalation port 40.

Referring now to FIGS. 6 & 7, an alternative indicator assembly for use with the invention is depicted. Inner frame 64 is provided with baffles 110 and apertures 112. Inner frame 64 and outer frame 118 are adapted so that the inside diameter of outer frame 118 is larger than the outside diameter of inner frame 64. The combination works so that indicator strip 82 and filter barrier 84 fit between inner frame 64 and outer frame 118. Outer frame 118 has baffles 114 and apertures 116 that cooperate with baffles 110 and apertures 112 of inner frame 64 to provide improved flow-through of gasses.

Figure 8:
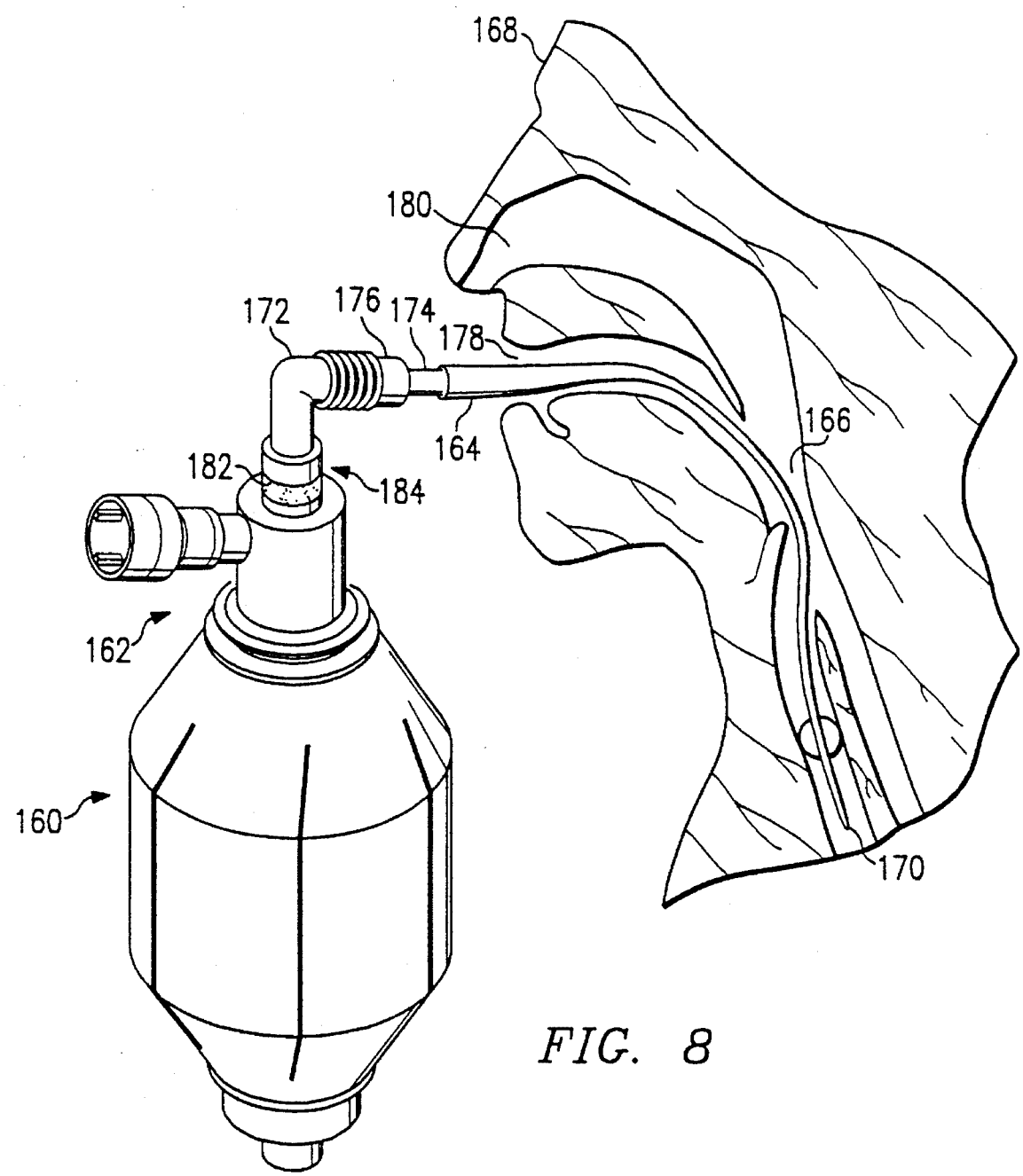
FIG. 8 illustrates the use of the present invention as an intubation device.

Referring now to FIG. 8, a resuscittor 160 incorporating a regulator 162 is connected to an endotracheal tube 164 for insertion into the trachea 166 of a patient 168. The tube has a tapered end 170 to ease insertion into the trachea 166 of patent 168. The tube 164 is connected to elbow 172 at connector 174 by adaptor 176. The endotracheal tube 164 may be inserted into the trachea 166 of the patient 168 through any of the mouth 178, the nasal cavity 180 or a cricoid membrane puncture (not shown). Indicator strip 182 of indicator assembly 184 reveals by change of color whether the endotracheal tube 164 is properly inserted into the patient's trachea 166.

Figure 9:
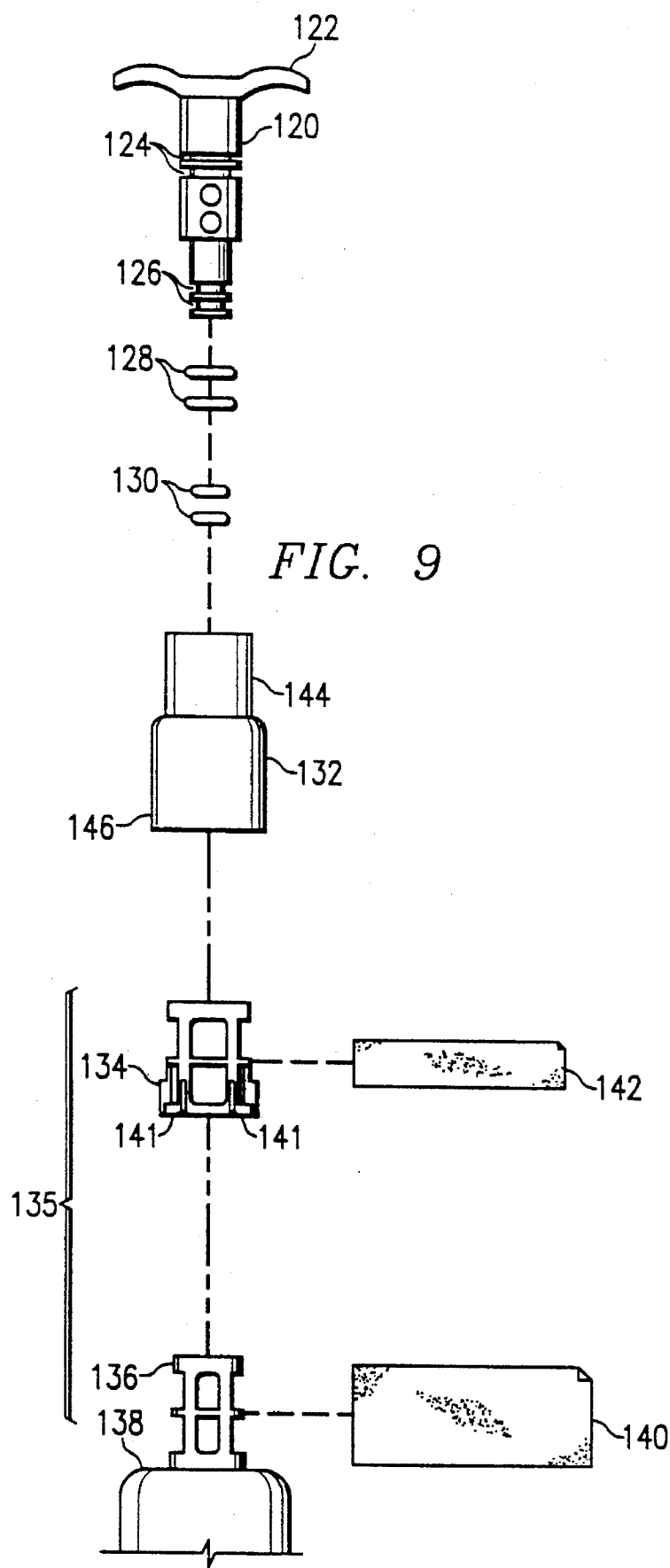
FIG. 9 is an alternative embodiment of the present invention illustrating a plug for use with the invention.

Referring now to FIG. 9, an exploded view of an alternative embodiment of the present invention is shown illustrating a unique means for providing indicator assembly 135 and a unique plug for isolating indicator strip 142 from the atmosphere while not in use. Plug 120 has handle 122 adapted for easy withdrawal and insertion. Plug 120 has recesses 124 and 126 adapted for receiving O-rings 128 and 130. Cap 132 is adapted to fit over outer-support frame 134 and inner-support frame 136 and to mate sealingly with regulator cap 138. Inner-support frame 136 is adapted to receive filter 140 which is press fit into place by outer-support frame 134. Outer-support frame 134 is adapted to receive indicator element 142 using shoulders 141. When filter 140 is assembled to inner-support frame 136 and indicator element 142 is assembled to outer-support frame 134 which, is then placed over innerframe 136 and capped by cap 132, a rapid response $CO_2$ indicator is provided directly in line with a breathing circuit to indicate the presence of respiration in a patient.

Still referring to FIG. 9, cap 132 has a tapered upper portion 144 and an expanded lower portion 146. Tapered upper portion 144 is adapted to mate sealingly with plug 120 and to isolate indicator element 142 from the atmosphere. When the entire assembly of FIG. 9 is put together and the plug 120 inserted through cap 132, the O-rings 128 fitted for recesses 124 isolate indicator element 142 at the top of cap 132 and O-rings 130 fitted into recesses 126 isolate indicator element 142 at the bottom of cap 132 providing for a tight fit and complete isolation from the atmosphere. Both O-rings 128, 130 fit inside inner-support frame 136.

Figure 10:
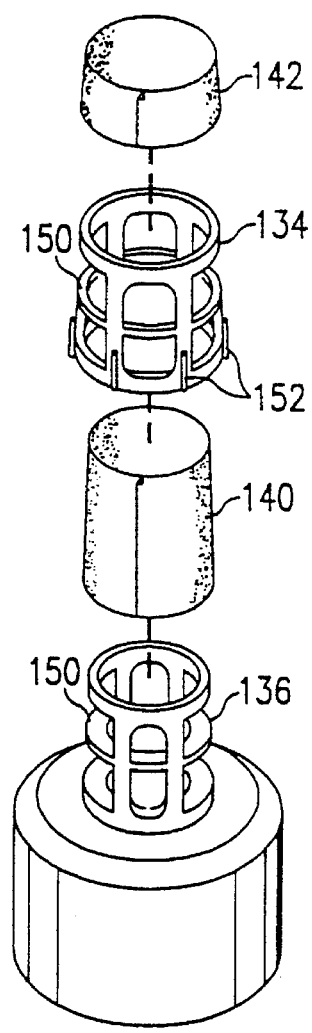
FIG. 10 illustrates an alternative embodiment of an indicator assembly for use with the present invention.

Referring now to FIG. 10, an alternative embodiment is shown of inner-support frame 136 and outer-support frame 134 with indicator element 142 and filter 140 assembled in place for positioning in a resuscitator. Both outer-support frame 134 and inner-support frame 136 are provided with baffles 150. Outer-support frame 134 is provided with support shoulders 152 for placing indicator element 142 so that it is positioned for maximum exposure to exhaled gasses.

From the above description, it will be seen by those having skill in the art that under the present invention, a resuscitator is provided with an integral carbon dioxide detector for indicating the presence of carbon dioxide in a patient's exhaled gas. Furthermore, a resuscitator with a carbon dioxide indicator is provided having a unique plug arrangement that provides for sealing the indicator from the atmosphere while in storage. While the invention has been particularly shown and described with reference to a preferred embodiment, it will be understood by those skilled in the art that various other changes in form and detail may be made without departing from the spirit and scope of the invention.

What is claimed is:

1. A resuscitator comprising:

a flexible container for supplying gas to a patient having outlet and inlet openings;

a regulator having a respiratory passageway for passing both fresh and exhaled gases fixed at one end to said outlet opening and having an inhalation port, an exhalation port and a viewing window;

a control valve located in said respiratory passageway over said outlet opening for controlling fresh gas flow to a patient through said inhalation port;

means for detecting carbon dioxide in exhaled gas from said patient, said detecting means located in said respiratory passageway adjacent to said viewing window such that said detecting means is exposed to fresh and exhaled gasses so as to provide an indication of the condition of the patient on each breath;

a plug for isolating said carbon dioxide detector from the atmosphere; and scavenging means associated with said plug for absorbing carbon dioxide.

2. The resuscitator of claim 1 further comprising valve means located between said inhalation and exhalation ports for preventing the mixing of said fresh and exhaled gasses.

3. The resuscitator of claim 1 wherein said scavenging means is soda lime.

4. A resuscitator comprising:

a flexible container for supplying gas to a patient having outlet and inlet openings;

a control valve housing fixed to said outlet opening of said container having an inhalation port, an exhalation port and a viewing window;

a control valve located in said housing over said outlet opening for controlling flow of fresh gas to a patient through said inhalation port;

means for detecting carbon dioxide in exhaled gas from said patient prior to entering said exhalation port and located in said viewing window of said housing such that said detecting means is exposed to both fresh and exhaled gas;

sealing means affixed to said exhalation port for preventing said carbon dioxide detector from being exposed to fresh gas during storage of said resuscitator; and scavenging means associated with said sealing means for absorbing carbon dioxide.

5. The resuscitator of claim 4 wherein said sealing means is a plug.

6. A resuscitator comprising:

a flexible container for supplying gas to a patient;

a regulator, fixed to said flexible container, having a respiratory passageway, an inhalation port, an exhalation port and a viewing window;

a control valve, located in said respiratory passageway of said regulator and communicating with said flexible container, for controlling fresh gas flow to a patient through said inhalation port; and means for detecting carbon dioxide in exhaled gas from said patient, said detecting means located in said respiratory passageway adjacent to said viewing window such that said detecting means is exposed to fresh and exhaled gasses;

a plug for isolating said carbon dioxide detector from the atmosphere; and scavenging means associated with said plug for absorbing carbon dioxide.

7. The resuscitator of claim 6 further comprising valve means located between said inhalation and exhalation ports for preventing the mixing of said fresh and stale gasses.

8. The resuscitator of claim 6 wherein said scavenging means is soda lime.

* * * * *